United States Patent [19]

Shah et al.

[11] Patent Number: 5,773,031
[45] Date of Patent: Jun. 30, 1998

[54] ACETAMINOPHEN SUSTAINED-RELEASE FORMULATION

[75] Inventors: Shirish A. Shah; Chris Y. Ho, both of Kalamazoo, Mich.

[73] Assignee: L. Perrigo Company, Allegan, Mich.

[21] Appl. No.: 608,839

[22] Filed: Feb. 27, 1996

[51] Int. Cl.$^6$ .............................. A61K 9/14; A61K 47/32
[52] U.S. Cl. ........................................... 424/497; 424/468
[58] Field of Search ................................. 424/490, 497, 424/468

[56] References Cited

U.S. PATENT DOCUMENTS

| | | |
|---|---|---|
| 3,424,842 | 1/1969 | Nürnberg . |
| 3,629,393 | 12/1971 | Nakamoto et al. . |
| 3,883,647 | 5/1975 | Geller . |
| 3,927,205 | 12/1975 | Ohno et al. . |
| 4,234,565 | 11/1980 | Flodin et al. . |
| 4,341,759 | 7/1982 | Bogentoft et al. . |
| 4,439,453 | 3/1984 | Vogel . |
| 4,526,777 | 7/1985 | Blume et al. . |
| 4,574,080 | 3/1986 | Roswall et al. . |
| 4,606,909 | 8/1986 | Bechgaard et al. . |
| 4,666,703 | 5/1987 | Kopf . |
| 4,695,467 | 9/1987 | Uemura et al. . |
| 4,708,874 | 11/1987 | De Haan et al. . |
| 4,710,519 | 12/1987 | Finnan et al. . |
| 4,716,041 | 12/1987 | Kjørnaes et al. . |
| 4,724,148 | 2/1988 | Sonobe et al. . |
| 4,729,190 | 3/1988 | Lee . |
| 4,740,365 | 4/1988 | Yukimatsu et al. . |
| 4,748,023 | 5/1988 | Tamàs et al. . |
| 4,765,988 | 8/1988 | Sonobe et al. . |
| 4,772,475 | 9/1988 | Fukui et al. . |
| 4,814,178 | 3/1989 | Bolton et al. . |
| 4,816,264 | 3/1989 | Phillips et al. . |
| 4,820,522 | 4/1989 | Radebaugh et al. . |
| 4,839,177 | 6/1989 | Colombo et al. . |
| 4,867,984 | 9/1989 | Patel . |
| 4,867,987 | 9/1989 | Seth . |
| 4,892,742 | 1/1990 | Shah . |
| 4,900,557 | 2/1990 | Dell et al. . |
| 4,940,586 | 7/1990 | Sparks et al. . |
| 4,952,402 | 8/1990 | Sparks et al. . |
| 4,968,509 | 11/1990 | Radebaugh et al. . |
| 4,971,805 | 11/1990 | Kitanishi et al. . |
| 4,981,693 | 1/1991 | Higashi et al. . |
| 4,983,401 | 1/1991 | Eichel et al. . |
| 5,004,613 | 4/1991 | Radebaugh et al. . |
| 5,011,694 | 4/1991 | Nuernbert et al. . |
| 5,015,479 | 5/1991 | Mulligan et al. . |
| 5,026,709 | 6/1991 | Harwood et al. . |
| 5,051,262 | 9/1991 | Panoz et al. . |
| 5,055,306 | 10/1991 | Barry et al. . |
| 5,073,380 | 12/1991 | Babu et al. . |
| 5,085,865 | 2/1992 | Nayak . |
| 5,093,200 | 3/1992 | Watanabe et al. . |
| 5,095,054 | 3/1992 | Lay et al. . |
| 5,128,142 | 7/1992 | Mulligan et al. . |
| 5,130,140 | 7/1992 | Urban et al. . |
| 5,160,737 | 11/1992 | Friedman et al. . |
| 5,167,964 | 12/1992 | Muhammad et al. . |
| 5,186,943 | 2/1993 | Okada et al. . |
| 5,198,228 | 3/1993 | Urban et al. . |
| 5,200,193 | 4/1993 | Radebaugh et al. . |
| 5,202,159 | 4/1993 | Chen et al. . |
| 5,229,134 | 7/1993 | Mention et al. . |
| 5,252,341 | 10/1993 | Sauerbier et al. . |
| 5,262,169 | 11/1993 | Sauerbier et al. . |
| 5,275,824 | 1/1994 | Carli et al. . |
| 5,275,825 | 1/1994 | Okada et al. . |
| 5,310,558 | 5/1994 | Pozzi et al. . |
| 5,316,774 | 5/1994 | Eury et al. . |
| 5,324,717 | 6/1994 | Berglindh et al. . |
| 5,324,718 | 6/1994 | Loftsson . |
| 5,330,766 | 7/1994 | Morella et al. . |
| 5,342,627 | 8/1994 | Chopra et al. . |
| 5,358,718 | 10/1994 | Sauerbier et al. . |
| 5,368,861 | 11/1994 | Ushimaru et al. . |
| 5,370,878 | 12/1994 | Shah . |
| 5,374,430 | 12/1994 | Newton et al. . |
| 5,378,474 | 1/1995 | Morella et al. . |
| 5,384,130 | 1/1995 | Kamada . |
| 5,451,409 | 9/1995 | Rencher et al. ....................... 424/468 |
| 5,489,436 | 2/1996 | Hoy et al. . |

FOREIGN PATENT DOCUMENTS

| | | |
|---|---|---|
| 2209280 | 10/1989 | United Kingdom . |
| 2253348 | 9/1992 | United Kingdom . |
| 9317673 | 9/1993 | WIPO . |

OTHER PUBLICATIONS

United Kingdom Search Report.

*Primary Examiner*—Peter F. Kulkosky
*Attorney, Agent, or Firm*—Price, Heneveld, Cooper, Dewitt & Litton

[57] ABSTRACT

An orally administrable sustained-release dosage form includes particles of an active pharmaceutical ingredient which is coated with a polymeric material that is water-insoluble, but water-permeable and water-swellable, so that the sustained-release dosage form provides controlled release which is independent of certain variable physiological factors such as pH. In accordance with one aspect of the invention, the active pharmaceutical ingredient is acetaminophen and the coated acetaminophen particles are combined with uncoated acetaminophen particles to provide a combination immediate-release/sustained-release dosage form. In accordance with another aspect of the invention, the active pharmaceutical ingredient is coated with a methacrylate ester copolymer, and the coated particles are combined with uncoated particles of an active pharmaceutical ingredient to provide a combination immediate-release/sustained-release dosage form, wherein the sustained-release component provides a release rate which is substantially independent of physiological factors such as pH. The final orally administrable dosage form can be appeared as compressed tablets, capsules or pouches.

7 Claims, No Drawings

ACETAMINOPHEN SUSTAINED-RELEASE FORMULATION

BACKGROUND OF THE INVENTION

This invention relates to sustained-release pharmaceutical formulations, and more particularly to oral acetaminophen sustained-release formulations for providing extended therapeutic relief.

Many medical conditions are best treated by administration of a pharmaceutical in such a way as to sustain its action over an extended period of time. For example, this kind of pharmaceutical administration can be useful for treating chronic pain, such as that associated with rheumatic or arthritic conditions. Sustained-release dosage forms can also be used beneficially in the administration of antiarrythmics, antihypertensives and other drugs whose sustained action is important to their efficacy.

Many physiological factors influence both the gastrointestinal transit time and the release of a drug from a controlled release dosage form, and thus influence the uptake of the drug into the systemic circulation. Dosage forms should therefore be designed so that such variable factors do not compromise the efficacy and safety of the product. Ideally, such sustained-release dosage forms should release the active pharmaceutical ingredient at a controlled rate such that the amount of active pharmaceutical ingredient which is available in the body to treat the condition is maintained at a relatively constant level over an extended period of time. That is, it is desirable that active pharmaceutical ingredient be released at a reproducible, predictable rate which is substantially independent of physiological factors which can vary considerably among different individuals and even over time for a particular individual.

The release of active pharmaceutical ingredient from a controlled release dosage form is generally controlled either by diffusion through a coating, diffusion of the agent from a monolithic device, or by erosion of a coating by a process which is dependent upon enzymes or pH. Because such factors can vary from time to time for a particular individual, and can also vary from one individual to another, enzymes or pH dependent sustained-release pharmaceutical formulations do not provide a reproducible rate of release of the active pharmaceutical ingredient, and thus do not minimize intra-subject and inter-subject variation in bio-availability of the active ingredient.

Certain medical conditions are most desirably treated with dosage form which provides both immediate and extended therapeutic effect while reducing the number of doses necessary, thereby making therapy more convenient. Known examples of pharmaceutical formulations which provide both immediate and sustained-release of an active pharmaceutical ingredient are disclosed in U.S. Pat. No. 4,574,080 to Roswall et al. and U.S. Pat. No. 4,971,805 to Kitanishi et al. Each of these patents disclose a pharmaceutical formulation comprised of a quick releasing component and a slow releasing component, wherein release of the active pharmaceutical ingredient from the slow releasing component relies on a pH dependent diffusion control mechanism such as an enteric coating. Such formulations have the disadvantage of releasing the active pharmaceutical ingredient at a variable rate dependent upon the pH of the gastrointestinal fluids in which it is contacted, which can vary from subject to subject and can vary for a particular subject.

U.S. Pat. No. 4,666,703 to Kopf discloses a quick-disintegrating pharmaceutical tablet containing an active substance in a granular delayed release form comprising a pharmaceutically active substance in granular form which is coated with a mixture of a polyacrylate, such as an aqueous dispersion of an ethyl acrylate-methyl methacrylate copolymer, and ethyl cellulose, which are subsequently compressed into tablets. Kopf, however, does not provide both immediate and sustained-release of the active pharmaceutical ingredient.

Roswall et al. (U.S. Pat. No. 4,574,080) discloses a pharmaceutical orally administrable controlled release multiple-units formulation form in which individual units comprise coated cores containing an active substance which is subjected to controlled release as a result of coating the cores with a water-insoluble, but water-diffusible controlled release coating. The units include instant release particles of an active substance adhered to the surface of a controlled release coating, the particles being at least one power of 10 smaller than the coated core.

U.S. Pat. No. 5,055,306 to Barry et al. discloses a pharmaceutical tablet comprised of granules having a core including an active substance and an encapsulating coating comprising 100 parts by weight of water-swellable acrylic polymer and 20 to 70 parts of water-soluble hydroxylated cellulose derivative. The combination of water-swellable acrylic polymer and water-soluble hydroxylated cellulose derivative provides a coating having release characteristics which are pH dependent, i.e. an enteric coating.

A two layer acetaminophen tablet is available in which one layer is comprised of uncoated, quick release acetaminophen particles, and the other layer is comprised of sustained release acetaminophen. Two compression steps are required to make the tablet, and the sustained release coating is pH dependent.

SUMMARY OF THE INVENTION

The present invention comprises a mixture of polymeric coated, sustained release acetaminophen particles and uncoated, quick release acetaminophen particles pressed together in a tablet. Preferably, the coating is water permeable, but is not soluble or pH dependent.

In another aspect of the invention, other pharmaceutical agents can be substituted for acetaminophen in the foregoing mixture, using the water permeable, water-insoluble, pH independent coating. Finally, the invention alternatively encompasses acetaminophen in sustained release form per se, coated with said water permeable, water-insoluble, pH independent coating.

DESCRIPTION OF THE PREFERRED EMBODIMENTS

In accordance with a first embodiment of the invention, a sustained-release acetaminophen formulation is provided. The acetaminophen is preferably provided in a finally divided form such as small particles or granules. The acetaminophen particles preferably have an average particle size between about 180 microns to 425 microns. The acetaminophen particles may contain excipients, adjuvants or other active ingredients in minor amounts if desired, but are more preferably comprised of at least 80, 90 or 95% acetaminophen.

The sustained-release acetaminophen formulations, in accordance with the first aspect of the invention, are provided with a sustained-release coating formulation comprising a water-insoluble, water-permeable and slightly water-swellable polymer coating. The polymeric coating is not soluble in the gastrointestinal fluids and is not sensitive to the pH thereof. The term "pH independent" as used herein means that the water permeability of the coating, and hence its ability to release pharmaceutical ingredients, is not a function of pH or is only very slightly dependent on pH. Accordingly, the sustained-release acetaminophen formulations of the present invention are capable of releasing acetaminophen into the gastrointestinal tract at a controlled rate which is independent of physiological factors such as pH, which can vary from one subject to another and can vary from time to time for a particular subject. The polymeric coating preferably comprises a methacrylate ester copolymer having the general formula:

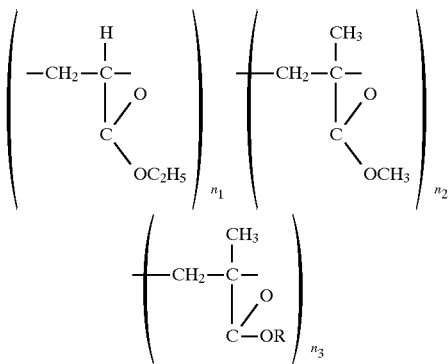

wherein R is an alkyl or aminoalkyl group having from 1 to about 12 carbon atoms, and wherein $n_1$, $n_2$, and $n_3$ are selected so that the polymer has a molecular weight of from about 100,000 to about 1,000,000. The ratio $n_1:n_2$ is from about 1:2 to about 2:1, and the ratio of $n_3:(n_1+n_2)$ is from about 0 to about 1:15. Particularly preferred are copolymers of ethylacrylate and methylmethacrylate, although terpolymers and other polymers comprising three or more different monomeric units having property similar to ethylacrylate-methylenethacrylate copolymers are also preferred. The preferred methacrylate-ethylacrylate copolymer has a molecular weight of approximately 800,000. A particularly preferred methylmethacrylate-ethylacrylate copolymer is Eudragrit® NE30D which is commercially available from R öhm Pharma.

The polymeric film coating can be applied to the acetaminophen particles in any suitable manner. Preferably, the polymeric film is applied as a uniform coating having a smooth surface structure and a relatively constant thickness. A particularly preferred method of applying the polymeric coating to the acetaminophen particles is by utilizing pneumatic spray guns. The pneumatic spray guns preferably have a nozzle diameter of from about 0.8 mm to about 2 mm, and are operated at an air pressure of from about 0.5 to about 3 bar. The spraying rate of the spray guns can be easily regulated using peristaltic pumps or pressure vessels. Ideally, spraying should be continuous with simultaneous drying so that the particles do not become too moist (over wet). The freshly sprayed polymeric film should dry as quickly as possible to avoid a agglomeration of the particles. Fluidized-bed processes are particularly suitable for coating small particles. For example fluidized-bed systems such as Aeromatic, Glatt with Wuster HS Column operate in closed cylindrical apparatuses into which an air stream is introduced from below to fluidized the acetaminophen particles and dry the films during spraying. In addition to fluidized-bed processes, modified coating drums (usually cylindrical horizontally rotating units with a perforated wall) are also suitable for coating small particles.

The acetaminophen particles having a polymeric controlled release coating can be further manufactured into various types of oral dosage forms. For example, the release coated acetaminophen particles can be compressed, either alone or in combination with excipients, adjuvants and/or other active ingredients, into pills, tablets or the like. As another example, the release coated particles can be loaded into capsules such as either soft gelatin capsules or hard gelatin capsules. As another example, the release coated particles can be packaged into a pouch with other active or inactive ingredients. It can be dispersed into water in form of suspension.

The coating composition may include minor amounts of emulsifiers, wetting agents and stabilizers such as isononylphenylpolyoxethylene glycol ethers. Minor amounts of talc can also be incorporated into the coating composition or subsequently applied to improve or enhance the flow properties of the coated particles.

Suitable coating thicknesses can range from about 2 micrometers to about 15 micrometers, depending on the desired diffusion properties. The weight of the coating is generally between 2 and 15% of the weight of the acetaminophen particles.

In accordance with another embodiment of the invention, the release coated acetaminophen particles can be combined with uncoated acetaminophen particles to provide an orally administrable pharmaceutical formulation having both immediate-release and sustained-release components. The uncoated acetaminophen particles may generally have substantially the same characteristics as the release coated particles prior to coating. As with the release coated particles, the uncoated particles may contain minor amounts of excipients, adjuvants and/or other active ingredients.

In the broader aspects of the invention, a variety of other release-coatings, including soluble, insoluble, permeable, impermeable or bio-degradable coatings, can be substituted the water-insoluble, water-permeable and water-swellable polymer coatings previously set forth. The polymer coating can be comprised of one or more polymers, including copolymers, terpolymers and other polymers having three or more different monomeric units. The polymers may include natural or synthetic polymers. Natural polymers which may be utilized in the sustained-release coating include polypeptides, polysacarides and alginic acid. Representative synthetic polymers include aqueous cellulose, hydroxyacyl cellulose, cellulose ether, cellulose esters, nitrocellulose, polymers of acrylic and methacrylic acids and esters thereof, polyamides, polycarbonates, polyalkylenes, polyalkylene glycol, polyalkylene oxides, polyalkylene terephalates, polyvinyl alcohols, polyvinyl ethers, polyvinyl esters, polyvinyl halides, polyvinyl pyrrolidone, polyglycolides, polysiloxanes and polyurethanes and copolymers thereof.

Particular examples of suitable polymers for use in the sustained-release coating of the combined immediate-release/sustained-release acetaminophen formulations includes: methyl cellulose, ethyl cellulose, hydroxypropyl cellulose, hydroxpropylmethyl cellulose, hydroxybutylmethyl cellulose, cellulose acetate, cellulose propionate (lower, medium or higher molecular weight), cellulose acetate propionate, cellulose acetate butyrate, cellulose acetate phthalate, carboxymethyl cellulose, cellulose triacetate, cellulose sulphate sodium salt, polymethylmethacrylate, polyethylmethacrylate, polybutymethacrylate, polybutymethacrylate, polyisobutymethacrylate, polyhexomethacrylate, polyisodecylmethacrylate, poly(lauryl methacrylate), poly(phenyl methacrylate), polymethalacrylate, polyisopropylacrylate, polyisbutalacrylate, polyoctadcylacrylate, polyethylene (low or high density), polypropolyne, polyethylene glycol, polyethylene oxide, polyethylene terephthalate, polyvinyl alcohol, polyvinyl isobutyl ether, polyvinyl acetate, polyvinyl chloride and polyvinyl pyrrolidone. Examples of suitable copolymers include: butylmethacrylate/isobutylmethacrylate copolymer, high molecular weight, methylvinyl ether/maleic acid copolymer, methylvinyl ether/maleic acid, monoethyl ester copolymer, methylvinyl ether/malec and anhydride copolymer and vinyl alcohol/vinyl acetate copolymer. Examples of suitable biodegradable polymers include: polylactides, polyglycolides, polyethylene terathatic and polyeurathine. Examples of suitable acrylate and methacrylate are polyacrylic and methacrylic polymer such as those sold under the trademark Eudragit®.

The combination immediate-release/sustained-release acetaminophen formulation can be comprised of substantially any amount of acetaminophen in immediate-release form which is effective and non-toxic, and any amount of acetaminophen in sustained-release form which is therapeutically effective and non-toxic over the sustained-release period when used in combination with the selected quantity of immediate-release acetaminophen. Specific examples include about 162.5 milligrams of acetaminophen in sustained release form, in combination with approximately 487.5 milligrams of acetaminophen in immediate-release form. Another specific example comprises about 325 milligrams of acetaminophen in immediate-release form, and about 325 milligrams of acetaminophen in sustained-release form.

The uncoated and coated acetaminophen particles can be combined in various oral pharmaceutic dosage forms or formulations such as capsules, tablets, pouches or the like. The sustained-release coated acetaminophen particles and the uncoated acetaminophen particles can be combined with various excipients, adjuvents, and/or other active ingredients.

Another embodiment of the invention includes particles of an active pharmaceutical ingredient which are coated with a water-insoluble, water-permeable, and slightly water-swellable polymeric coating which provides diffusion controlled sustained-release of the active ingredient at a highly reproducible, predictable rate which is independent of inter- and intra-subject physiological variations such as pH, combined with an uncoated pharmaceutically active ingredient which can be the same or different from the sustained-release coated pharmaceutically active ingredient. The resulting combined immediate-release/sustained-release formulation provides higher reproduciability of drug release rates than other sustained-release dosage forms utilizing conventional enteric sustained-release coating compositions, while providing, both immediate and sustained-release of medicaments.

Examples of such other active ingredients include antacids, anti-inflammatory substances, coronary dilators, cerebral dilators, peripheral vasodilators, anti-infectives, psychotropics, anti-maniics, stimulants, anti-histamines, laxatives, decongestants, vitamins, gastro-intestinal sedatives, anti-diarrheal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics and anti-uricemic drugs. Typical active ingredients include gastro-intestinal sedatives such as metoclopramide and propantheline bromide; antacids such as aluminium trisilcate, aluminium hydroxide and cimetidine; anti-inflammatory drugs such as phenylbutazone, indomethacin, naproxen, ibuprofen, fluriprofen, diclofenac, dexamethasone, prednisone and prednisolone; coronary vasodilator drugs such as glyceryl trinitrate, isosorbide dinitrate and pentaerythritol tetranitrate; peripheral and cerebral vasodilators such as solocidilum, vincamine, naftidrofuryl oxalate, co-dergocrine mesylate, cyclandelate, papaverine and nicotinic acid; anti-infective substances such as erythromycin stearate, cephalexin, nalidixic acid, tetracyline hydrochloride, ampicillin, flucloxacillin sodium, hexamine mandelate and hexamine hippurate; neuroleptic drugs such as flurazepam, diazepam, temazepam, amitryptyline, dioxepin, lithium carbonate, lithium sulfate, chlorpromazine, thioridazine, trifluoperazine, fluphenazine, piperothiazine, haloperidol, maprotiline hydrochloride, imipramine and desmethylimipramine; central nervous stimulants such as methlylphenidate ephedrine, epinephrine, isoproterenol, amphetamine sulfate and amphetaminc hydrochloride; anti-histamic drugs such as diphenhydramine, diphenylpyraline, chlorpheniramine and brompheniramine; laxative drugs such as bisacodyl and magnesium hydroxide; dioctyl sodium sulfosuccinate; nutritional supplements such as ascorbic acid, alpha tocopherol, thiamine and pyridoxine; anti-spasmodic drugs such as dicyclomine and diphenoxylate; drugs affecting the rhythm of the heart such as verapamil, nifedipine, diltiazem, procainamide, disopyramide, bretylium tosylate, quinidine sulfate and quinidine gluconate; drugs used in the treatment of hypertension such as propranolol hydrochloride, guanethidine monosulphate, methyldopa, oxprenolol hydrochloride, captopril and hydralazine; drugs used in the treatment of migraine such as ergotamine; drugs affecting coagulability of blood such, as epsilon aminocaproic acid and protaminc sulfate; analgesic drugs such as acetylsalicylic acid, acetaminophen, codeine phosphate, codeine sulfate, oxycodone, dihydrocodeine tartrate, oxycodeinone, morphine, heroin, nalbuphine, butorphanol tartrate, pentazocine hydrochloride, cyclazacine, pethidine, buprenorphine, and mefenamic acid; anti-epileptic drugs such as phenytoin sodium and sodium valproate; neuromuscular drugs such as dantrolene sodium; substances used in the treatment of diabetes such as tolbutamide, disbenase glucagon and insulin; drugs used in the treatment of thyroid gland disfunction such as triiodothyronine, thyroxine and propylthiouracil, diuretic drugs such as furosemide, chlorthalidone, hydrochlorothiazide, spironolactone and triamterene; the uterine relaxant drug ritodrine; appetite suppressants such as fenfluramine hydrochloride, phentermine and diethylproprion hydrochloride; anti-asthmatic and bronchodilator drugs such as aminophylline, theophylline, salbutamol, orciprenaline sulphate and terbutaline sulphate; expectorant drugs such as guaiphenesin; cough suppressants such as dextromethorphan and noscapine; mucolytic drugs such as carbocisteine; anti-septics such as cetylpyridinium chloride, tyrothricin and chlorhexidine; decongestant drugs such as phenylpropanolamine and pseudoephedrine; hypnotic drugs such as dichloralphenazone and nitrazepam; anti-nauseant drugs such as promethazine theoclate, hemopoietic drugs such as ferrous sulphate, folic acid and calcium gluconate; uricosuric drugs such as sulphinpyrazone, allopurinol and probenecid.

While any of the above embodiments of the invention can be formulated into generally any of a variety of different types of orally administrable pharmaceutical dosage forms such as capsules, the pharmaceutical compositions of the invention are most preferably pressed into tablets, pills, or the like. The tablets preferably have the hardness of from about 11 to about 19 SCU, and most preferably a hardness of about 15 SCU. The tablets preferably have a friability of less than about 0.8% weight loss after 6 minutes.

Suitable excipients and adjuvants which can be used in the preparation of the sustained-release therapeutic compositions of the present invention generally include those conventionally used in the pharmaceutical industry. Examples include fillers and diluents such as lactose, sucrose, dextrose, mannitol, calcium sulphate, dicalcium sulphate, tricalcium sulphate, starches such as rice starch and micro-crystalline cellulose. Useful binders include acacia, tragacanth, gelatine, sucrose, pre-gelatinized starch, starch, sodium alginate, almonium calcium alginate, methylcellulose, sodium carboxymethyl cellulose, ethel cellulose, hydroxypropylmethyl cellulose, polyvinylpyrrolidone, mechanism aluminum ciliate and polyacrylamide. Examples of disintigrants include cross-linked polyvinylpyrrolidone, starch derivatives such as car-boxymethyl cellulose and cellulose derivatives. Lubricants, guidance and anti-adhesive agents include metallic stearates such as magnesium stearate, talc, high melting point waxes, and colordacylica.

For the various acetaminophen formulations disclosed herein, preferred combination disintigrants/binders include cross-linked polyvinylpyrrolidone such as Polyplasdone XL® available from GAF or croscarmellose sodium such as Ac-Di-Sol® available from FMC Corporation. Another disintigrants/binder which is preferably utilized in combination with the cross-linked polyvinylpyrrolidone or croscarmellose sodium is micro-crystalline cellulose. The preferred disintigrants/binders can be utilized in effective amounts which can be readily determined using known techniques.

The compositions of the invention are typically directly tableted using a conventional tableting apparatus e.g. a Manesty Rotary Press, a Stokes Rotary Press, etc., at a temperature of about 15° to about 30° C. and at a pressure of from about 0.4 to about 3.0 tons.

The tablets are desirably provided with a coating which helps prevent dusting of the tablets during handling and in the bottle, and which improves the appearance and swallowability of the tablets. A preferred tablet coating is set forth in the examples. The coated tablets are also preferably provided with an overcoat of carnauba wax which provides the tablets with an adhesived glossy appearance.

The following examples illustrate preferred combination in immediate-release/ sustained-release acetaminophen formulations in accordance with the invention.

EXAMPLE 1

A preferred combined immediate-release/sustained-release acetaminophen formulation containing 650 milligrams of acetaminophen is set forth in Table 1.

Tablets are prepared in accordance with the formulations set forth in Table 1 by mixing the micro-crystalline cellulose with sustained-release coated acetaminophen containing acetaminophen, isonunophinal polyoxiethylene glycol ethers, methacrylate ester copolymer and talc in the weight ratio of 20.790; 0.023; 1.531; 1.167. A suitable mixing time for the sustained-release coated acetaminophen particles and the micro-crystalline cellulose is about 1 minute. The mixture of coated acetaminophen and micro-crystalline cellulose are then preferably combined with the cross-linked polyvinylpyrrolidone and with the uncoated acetaminophen. The uncoated acetaminophen (Compap WSE 95%) is comprised primarily of acetaminophen, and contains minor amounts of maltodextrin (a filler) and polyvinylpyrrolidone (povidone). A suitable mixing time for the pre-mixed sustained-release coated acetaminophen and micocrystalline cellulose, uncoated acetaminophen, and cross-linked polyvinylpyrrolidone is about 10 minutes. Afterward, magnesium sturate is mixed in with the above ingredients. A suitable mixing time for the magnesium stearate with the above ingredients is about 3 minutes.

The above mixture is compressed into caplets having a weight of approximately 0.77 grams, a thickness of about 0.26 inches plus or minus 0.005 inches, a hardness of about 11 to 19 SCU (preferably about 15 SCU), a friability of no more than 0.8% weight loss after 6 minutes and an individual tablet weight variation of 0.732 to 0.8% grams.

The tablets can be coated by placing them in a 60 inch accela-cota pan, and spraying them with a coating such as opadry W-YS-1-7003.

EXAMPLE 2

Another preferred immediate-release/sustained-release acetaminophen formulation containing 3 milligrams of acetaminophen in immediate-release form and 325 milligrams of acetaminophen in sustained-release form per tablet is set forth in Table 2. The tablet prepared in accordance with the formulations set forth in Table 2 can be prepared in a manner substantially identical to the manner in which the tablet from Example 1 are prepared.

TABLE 1

TENTATIVE INGREDIENT DISCLOSURE
544XA EXTENDED RELIEF APAP 650 MG

| RAW MATERIAL | | INGREDIENT | LABEL CLAIM | % OF FORMULA |
|---|---|---|---|---|
| 7578R | APAP-SR | ACETAMINOPHEN, USP | 162.50 MG | 20.790 |
| 3520 | COMPAP WSE 95% | ACETAMINOPHEN, USP | 487.50 MG | 62.370 |
| 3075 | CARNAUBA WAX | CARNAUBA WAX, NF | | 0.010 |
| 8897 | CROSPOVIDONE XL | CROSPOVIDONE XL | | 1.970 |
| 8796 | OPADRY W-YS-1-7003 | HYDROXYPROPYLMETHYLCELLULOSE | | 0.883 |
| 7578R | APAP-SR | ISONOYLPHENYLPOLYOXETHYLENE GLYCOL ETHERS | | 0.023 |
| 3241 | MG STEARATE | MAGNESIUM STEARATE, NF | | 0.499 |
| 3520 | COMPAP WSE 95% | MALTODEXTRIN | | <3.305 |
| 7578R | APAP-SR | METHACRYLIC ACID COPOLYMERS | | 1.531 |
| 8871 | MICROCRYSTALLINE CELLULOSE | MICROCRYSTALLINE CELLULOSE | | 6.856 |

TABLE 1-continued

TENTATIVE INGREDIENT DISCLOSURE
544XA EXTENDED RELIEF APAP 650 MG

| RAW MATERIAL | | INGREDIENT | LABEL CLAIM | % OF FORMULA |
|---|---|---|---|---|
| 8796 | OPADRY W-YS-1-7003 | POLYETHYLENE GLYCOL 400 | | 0.118 |
| 8796 | OPADRY W-YS-1-7003 | POLYSORBATE 80, NF | | 0.115 |
| 3520 | COMPAP WSE 95% | POVIDONE, USP | | <3.305 |
| 7578R | APAP-SR | TALC #127 | | 1.167 |
| 8796 | OPADRY W-YS-1-7003 | TITANIUM DIOXIDE, USP | | 0.462 |
| | | | TOTAL | 100.000 |

TABLE 2

TENTATIVE INGREDIENT DISCLOSURE
544XB EXTENDED RELIEF APAP 650 MG

| RAW MATERIAL | | INGREDIENT | LABEL CLAIM | % OF FORMULA |
|---|---|---|---|---|
| 7578R | APAP-SR | ACETAMINOPHEN, USP | 325.00 MG | 41.580 |
| 3520 | COMPAP WSE 95% | ACETAMINOPHEN, USP | 325.00 MG | 41.580 |
| 3075 | CARNAUBA WAX | CARNAUBA WAX, NF | | 0.010 |
| 8897 | CROSPOVIDONE XL | CROSPOVIDONE XL | | 1.970 |
| 8796 | OPADRY W-YS-1-7003 | HYDROXYPROPYL METHYLCELLULOSE | | 0.883 |
| 7578R | APAP-SR | ISONOYLPHENYLPOLYOXETHYLENE GLYCOL ETHERS | | 0.050 |
| 3241 | MG STEARATE | MAGNESIUM STEARATE, NF | | 0.493 |
| 3520 | COMPAP WSE 95% | MALTODEXTRIN | | <2.188 |
| 7578R | APAP-SR | METHACRYLIC ACID COPOLYMERS | | 3.291 |
| 8871 | MICROCRYSTALLINE CELLULOSE | MICROCRYSTALLINE CELLULOSE | | 4.855 |
| 8796 | OPADRY W-YS-1-7003 | POLYETHYLENE GLYCOL 400 | | 0.118 |
| 8796 | OPADRY W-YS-1-7003 | POLYSORBATE 80, NF | | 0.115 |
| 3520 | COMPAP WSE 95% | POVIDONE, USP | | <2.188 |
| 7578R | APAP-SR | TALC #127 | | 2.506 |
| 8796 | OPADRY W-YS-1-7003 | TITANIUM DIOXIDE, USP | | 0.462 |
| | | | TOTAL | 100.000 |

It will become apparent to those skilled in the art that various modifications to the preferred embodiment of the invention is described herein can be made without departing from the spirit or scope of the invention as defined by the appended claims.

The embodiments of the invention in which an exclusive property or privilege is claimed are defined as follows:

1. An orally aministrable sustained-release dosage form, comprising a mixture of a pharmaceutically effective amount of uncoated acetaminophen particles and a pharmaceutically effective amount of acetaminophen particles coated with a polymeric material which is water-insoluble, said polymeric material being water-permeable, and wherein said polymeric material comprises a methacrylate ester copolymer.

2. The dosage form of claim 1, wherein said methacrylate ester copolymer has the general formula:

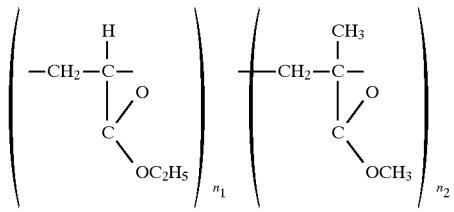

where R is an alkyl or aminoalkyl group having from 1 to about 12 carbon atoms, and wherein $n_1$, $n_2$ and $n_3$ are selected so that said methacrylate ester copolymer has a molecular weight of from about 100,000 to about 1,000,000.

3. The dosage form of claim 2, wherein the ratio of $n_1$, $n_2$ is from about 1:2 to about 2:1, and the ratio $n_3$: $(n_1+n_2)$ is at or below about 1:15.

4. The dosage form of claim 3, wherein said methacrylate ester copolymer is substantially comprised of methylmethacrylate and ethylacrylate.

5. The dosage of claim 4, wherein said methacrylate ester copolymer has a molecular weight of about 800,000.

6. The dosage form of claim 5, wherein said acetaminophen particles have an average size of from about 180 micrometers to about 425 micrometers.

7. The dosage form of claim 6, wherein said uncoated particles and said coated particles, prior to being coated, have an average size of from about 180 micrometers to about 425 micrometers.

* * * * *

UNITED STATES PATENT AND TRADEMARK OFFICE
CERTIFICATE OF CORRECTION

PATENT NO. : 5,773,031
DATED : June 30, 1998
INVENTOR(S) : Shirish A. Shah and Chris Y. Ho It is certified that error appears in the above-identified patent and that said Letters Patent is hereby corrected as shown below:

Abstract, line 20;

"can be appeared" should be --can appear--.

Column 1, line 29;

Before "active" insert "--an--.

Column 1, line 46;

After "with" insert --a--.

Column 3, lines 40-41;

"R öhm" should be --Röhm--.

Column 3, line 61;

"fluidized" should be --fluidize--.

Column 4, line 33;

After "substituted" insert --for--.

UNITED STATES PATENT AND TRADEMARK OFFICE
CERTIFICATE OF CORRECTION

PATENT NO. : 5,773,031
DATED : June 30, 1998
INVENTOR(S) : Shirish A. Shah and Chris Y. Ho It is certified that error appears in the above-identified patent and that said Letters Patent is hereby corrected as shown below:

Column 4, line 64;

"polymethalacrylate" should be --polymethacrylate--.

Column 4, line 66;

"polyoctadcylacrylate" should be --polyoctadecylacrylate--.

Column 4, line 67;

"polypropolyne" should be --polypropylene--.

Column 5, line 7;

"ether/malec" should be --ether/malic--.

Column 5, line 10;

"terathatic" should be --terephthalate--.

Column 5, line 10;

"polyeurathine" should be --polyurethane--.

Column 5, line 47;

"reproduciability" should be --reproducibility--.

UNITED STATES PATENT AND TRADEMARK OFFICE
CERTIFICATE OF CORRECTION

PATENT NO. : 5,773,031
DATED : June 30, 1998
INVENTOR(S) : Shirish A. Shah and Chris Y. Ho It is certified that error appears in the above-identified patent and that said Letters Patent is hereby corrected as shown below:

Column 5, line 55;

"anti-maniics" should be --anti-manic--.

Column 5, line 56;

"gastro-intestinal" should be --gastrointestinal--.

Column 6, line 1;

"gastro-intestinal" should be gastrointestinal--.

Column 6, line 37;

"protaminc" should be --protamine--.

Column 7, line 19;

"mechanism aluminum ciliate" should be --magnesium aluminum silicate--.

Column 8, line 10;

"isonunophinal polyoxiethylene" should be --nonylphenyl polyoxyethylene--.

Column 8, line 25;

"sturate" should be --stearate--.

UNITED STATES PATENT AND TRADEMARK OFFICE
CERTIFICATE OF CORRECTION

PATENT NO. : 5,773,031
DATED : June 30, 1998
INVENTOR(S) : Shirish A. Shah and Chris Y. Ho It is certified that error appears in the above-identified patent and that said Letters Patent is hereby corrected as shown below:

Column 8, line 33;

"0.732 to 0.8%" should be --0.732 to 0.809--.

Column 8, line 42;

"3 milligrams" should be --325 milligrams--.

Column 8, line 48;

"tablet" should be --tablets--.

Signed and Sealed this

Thirtieth Day of March, 1999

Attest:

*Attesting Officer*

Q. TODD DICKINSON

*Acting Commissioner of Patents and Trademarks*